US012616835B2

(12) United States Patent
Kim et al.

(10) Patent No.: US 12,616,835 B2
(45) Date of Patent: May 5, 2026

(54) NEUROSTIMULATION-BASED NEUROFEEDBACK DEVICE USING BRAIN WAVES AND HEARTBEAT SIGNALS

(71) Applicant: NeuroTx Co., Ltd, Seoul (KR)

(72) Inventors: Dong-Joo Kim, Seoul (KR); Young-Tak Kim, Seoul (KR); Hyun-Ji Kim, Seoul (KR)

(73) Assignee: NeuroTx Co., Ltd, Seoul (KR)

( * ) Notice: Subject to any disclaimer, the term of this patent is extended or adjusted under 35 U.S.C. 154(b) by 597 days.

(21) Appl. No.: 17/966,190

(22) Filed: Oct. 14, 2022

(65) Prior Publication Data

US 2023/0054459 A1 Feb. 23, 2023

(30) Foreign Application Priority Data

Aug. 17, 2021 (KR) ......................... 10-2021-0108017

(51) Int. Cl.
A61N 1/36 (2006.01)
A61B 5/024 (2006.01)
(Continued)

(52) U.S. Cl.
CPC .......... A61N 1/36031 (2017.08); A61B 5/024 (2013.01); A61B 5/369 (2021.01);
(Continued)

(58) Field of Classification Search
CPC .............. A61N 1/36031; A61N 1/0452; A61N 1/0456; A61N 1/36025; A61B 5/024;
(Continued)

(56) References Cited

U.S. PATENT DOCUMENTS

2007/0156182 A1* 7/2007 Castel ................ A61N 1/36034
607/2
2013/0030257 A1* 1/2013 Nakata .................... G01S 13/87
600/407

(Continued)

FOREIGN PATENT DOCUMENTS

KR 10-2004-0085440 A 10/2004

*Primary Examiner* — Unsu Jung
*Assistant Examiner* — Natasha Patel
(74) *Attorney, Agent, or Firm* — Sughrue Mion, PLLC

(57) ABSTRACT

Disclosed is a neurofeedback device, including a body attached to a user's body and configured to provide electrical stimulation to a vagus nerve region, wherein the body includes: a frame provided in a symmetrical and elliptical shape, wherein one side and another side in a longitudinal direction are concavely recessed toward a center, and attached to a user's neck; a vagus nerve stimulator located on a back surface of the frame, provided to include a plurality of electrodes for providing electrical stimulation to the vagus nerve region, and attached to skin directly above the vagus nerve region located next to carotid artery of the user; a heart rate sensor located at a center of left and right symmetry of the frame on a back surface of the frame and configured to detect heart rates of the user; a manipulator located in front of the frame and configured to receive a user's command; and a plurality of connection ports formed on a side surface of the frame to transmit and receive signals, wherein the plural electrodes of the vagus nerve stimulator are provided one by one on left and right sides in the symmetrical structure of the frame and, when the frame is attached to the user's skin, are disposed perpendicular to a direction of the vagus nerve.

6 Claims, 4 Drawing Sheets

(51) Int. Cl.
| | | |
|---|---|---|
| *A61B 5/369* | (2021.01) | |
| *A61N 1/04* | (2006.01) | |
| *A61M 21/02* | (2006.01) | |

(52) U.S. Cl.
CPC ......... *A61N 1/0452* (2013.01); *A61N 1/0456* (2013.01); *A61M 21/02* (2013.01); *A61N 1/36025* (2013.01)

(58) Field of Classification Search
CPC ..... A61B 5/369; A61B 5/02438; A61B 5/372; A61B 5/375; A61M 21/02; A61M 2021/0033; A61M 2021/005; A61M 2206/00; A61M 2230/06; A61M 2230/10; A61M 2021/0072
See application file for complete search history.

(56)                              References Cited

U.S. PATENT DOCUMENTS

| | | | | |
|---|---|---|---|---|
| 2015/0148878 | A1* | 5/2015 | Yoo ....................... | A61N 1/0456 607/148 |
| 2015/0335288 | A1* | 11/2015 | Toth ....................... | A61B 5/388 600/391 |
| 2017/0224990 | A1* | 8/2017 | Goldwasser ......... | A61N 1/0476 |
| 2018/0272118 | A1* | 9/2018 | Goldwasser ......... | A61N 1/0492 |
| 2019/0336765 | A1* | 11/2019 | Charlesworth .... | A61N 1/36034 |
| 2020/0001041 | A1* | 1/2020 | Kranck ................ | A61M 21/02 |
| 2020/0230408 | A1* | 7/2020 | Errico ............... | A61N 1/36014 |

\* cited by examiner

NEUROSTIMULATION-BASED NEUROFEEDBACK DEVICE USING BRAIN WAVES AND HEARTBEAT SIGNALS

CROSS-REFERENCE TO RELATED APPLICATION

This application claims priority to Korean Patent Application No. 1020210108017, filed on Aug. 17, 2021 in the Korean Intellectual Property Office, the disclosure of which is incorporated herein by reference.

BACKGROUND OF THE DISCLOSURE

Field of the Disclosure

The present disclosure relates to a neurostimulation-based neurofeedback device using brain waves and heartbeat signals, and more particularly to a neurostimulation-based neurofeedback device using brain waves and heartbeat signals to identify a user's brain and nervous system status in real-time and provide neurofeedback based on the identified brain and nervous system status.

Description of the Related Art

Normal sleep is essential for a healthy life, and sleep accounts for ⅓ of human lifespan. However, in modern times, it is known that more than 10% of adults suffer from sleep disorders due to various causes such as overwork, stress, aging, living environment and diseases and about one-third of adults experience sleep disorders in some form during their lifetime. Sleep disorders often appear as early symptoms of neuropsychiatric disorders, and some psychiatric disorders are accompanied by characteristic changes in sleep physiology. According to statistics from the US Sleep Association, 60% of Americans suffer from sleep disturbances from time to time, and according to the US Transportation Safety Board, these sleep disturbances cause about 1,000 car accidents each year, resulting in the death of more than 1,500 people. Thereby, sleep disorders are recognized as a serious social problem. In addition, lifestyle habits such as the increased use of smartphones in modern society are also pointed out as the cause of poor sleep.

In particular, it is known that sleep disorders caused by melatonin deficiency can be improved through vagus nerve stimulation wherein Locus Coeruleus (LC) is stimulated through Nucleus Tractus Solitarius (NTS) and LC promotes Norepinephrine (NE) secretion to stimulate Dorsal Raphe Nucleus (DRN), thereby increasing serotonin (5-HT) secretion and melatonin.

Accordingly, as a treatment method that stimulates the vagus nerve connected to the central nervous system to help the autonomic nerve function and the activity of the brain neural network, vagus nerve stimulation capable of improving cognitive function by promoting synaptic plasticity in the cerebral cortex and hippocampus, which controls cognitive functions, is being used.

This conventional neurostimulation technique is a method of providing only stimulation of a specific frequency (Hz) and intensity (mA) previously set. However, since a response to a stimulus varies according to the characteristics and condition of a user, it is impossible to provide suitable neurostimulation with the conventional fixed pattern stimulation, and such a limitation results in a problem in that the effect on vagal nerve stimulation is small.

RELATED ART DOCUMENT

Patent Document (Patent Document 1) Korean Patent Application Publication No. 10-2004-0085440

SUMMARY OF THE DISCLOSURE

Therefore, the present disclosure has been made in view of the above problems. One object of the present disclosure is to provide optimized personalized vagus nerve stimulation to a user during sleep based on autonomic nervous system activation information and real-time sleep stage classification results collected through brain waves and heart rate signals measured during sleep.

It is another object of the present disclosure to provide a neurostimulation-based neurofeedback device utilizing brain wave, heart rate and motion signals which can improve sleep disorders and prevent deterioration of cognitive function by providing the optimized personalized vagus nerve stimulation.

It is yet another object of the present disclosure to provide a neurostimulation-based neurofeedback device utilizing brain waves and heart rate signals which can improve symptoms of various diseases such as sleep disorders, anxiety disorders, and cognitive dysfunction by providing personalized vagus nerve stimulation through a solution of providing both monitoring and nerve stimulation.

In accordance with an aspect of the present disclosure, the above and other objects can be accomplished by the provision of a neurofeedback device, including a body attached to a user's body and configured to provide electrical stimulation to a vagus nerve region, wherein the body includes: a frame provided in a symmetrical and elliptical shape, wherein one side and another side in a longitudinal direction are concavely recessed toward a center, and attached to a user's neck; a vagus nerve stimulator located on a back surface of the frame, provided to include a plurality of electrodes for providing electrical stimulation to the vagus nerve region, and attached to skin directly above the vagus nerve region located next to carotid artery of the user; a heart rate sensor located at a center of left and right symmetry of the frame on a back surface of the frame and configured to detect heart rates of the user; a manipulator located in front of the frame and configured to receive a user's command; and a plurality of connection ports formed on a side surface of the frame to transmit and receive signals, wherein the plural electrodes of the vagus nerve stimulator are provided one by one on left and right sides in the symmetrical structure of the frame and, when the frame is attached to the user's skin, are disposed perpendicular to a direction of the vagus nerve.

Here, the neurofeedback device may further include a brain wave measure attached to a head of the user to measure brain waves of the user; and a first connection cable connected to one of the plural connection ports to connect the body and the brain wave measure to each other, wherein the brain wave measure includes: a first band configured to have a predetermined width and provided in a form of extending from around a user's neck and being attached over a part of a user's head past a back of a user's ear when connected to the body through the first connection cable; a patch-type first brain wave sensor located at one end of the first band and detachably attached to a part of the user's head to measure brain waves in a left prefrontal lobe Fp1 region of the user; a second brain wave sensor located at a rear end of the first brain wave sensor and detachably attached to the part of the user's head to measure brain waves in a right prefrontal lobe Fp2 region of the user; a reference electrode located at a rear end of the second brain wave sensor and detachably attached around the user's ear to provide a reference signal for brain wave measurement; a ground electrode located at a rear end of the reference electrode and detachably attached around the user's ear to provide a ground signal for brain wave measurement; and a first connector located at a rear end of the ground electrode and inserted into and connected to another end of the first connection cable.

In addition, a portion of the first band, on which the first brain wave sensor, the second brain wave sensor, the reference electrode and the ground electrode are disposed, may have a circular shape having a larger diameter than the predetermined width.

In addition, the first connection cable may include: a first cable; a first terminal located at one end of the first cable and provided with a protruding terminal to be inserted into one of the connection ports of the body; and a first socket located at another end of the first cable and configured to include a hole into which the first connector of the brain wave measure is to be inserted.

The neurofeedback device may further include a genioglossus muscle stimulator attached around the user's neck and configured to include an electrode for outputting electrical stimulation corresponding to a neurofeedback signal; and a neurofeedback device connected to one of the plural connection ports and configured to connect the body and the genioglossus muscle stimulator to each other.

In addition, the genioglossus muscle stimulator may include: a second band attached to skin directly above a genioglossus muscle region of the user when connected to the body through the second connection cable; a genioglossus muscle electrode located on a back surface of one end of the second band to provide the electrical stimulation to the user's genioglossus muscle region, and provided in a form of a patch to be attached to the skin directly above the genioglossus muscle; and a second connector located at another end of the second band to be inserted into and connected to the second connection cable.

In addition, the second connection cable may include: a second cable; a second terminal located at one end of the second cable and provided with a protruding terminal to be inserted into one of the connection ports of the body; and a second socket located at another end of the second cable and provided with a hole into which the second connector of the brain wave measure is to be inserted.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Figure 1:
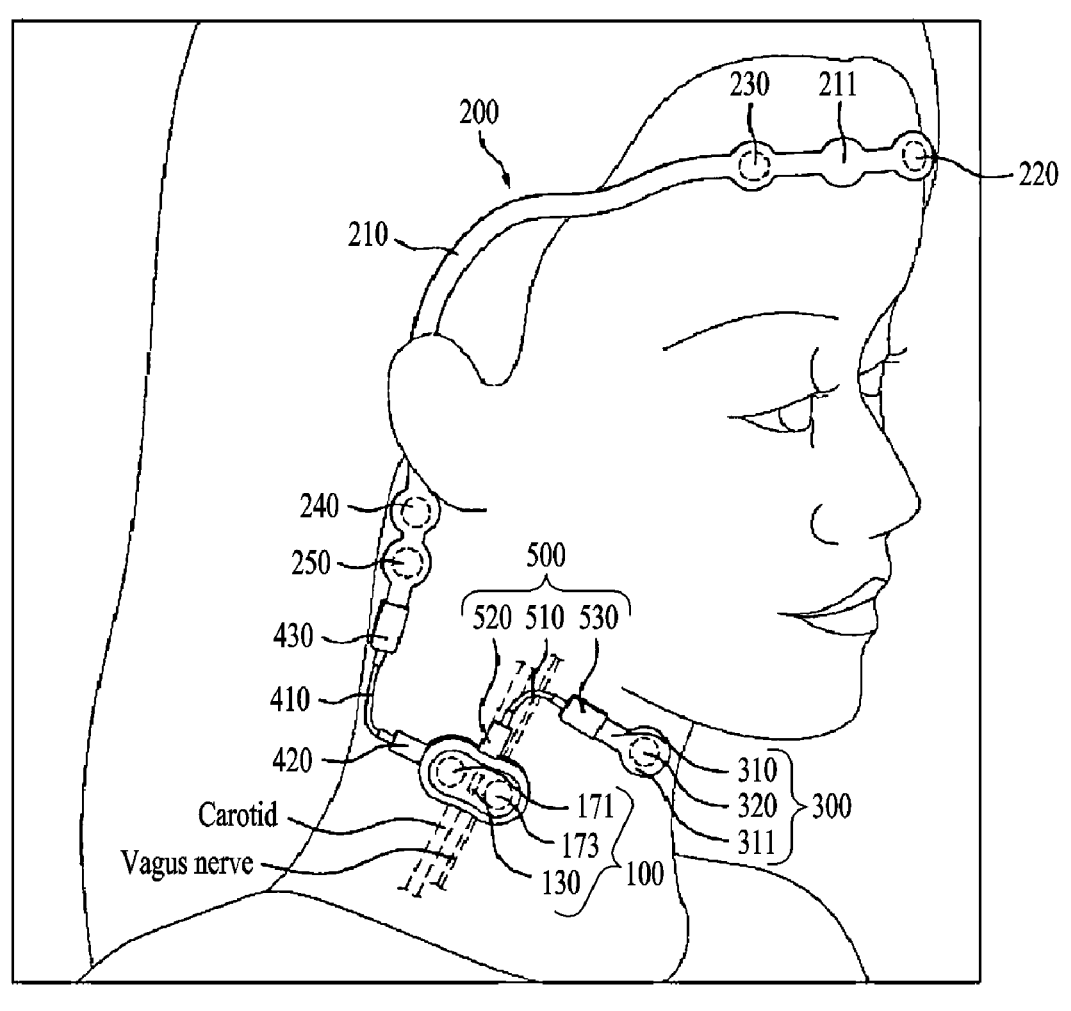
FIG. 1 is a diagram for explaining a state in which a user wears a neurofeedback device according to an embodiment of the present disclosure.

Hereinafter, specific embodiments of the present disclosure are described with reference to the attached drawings. These embodiments are described in sufficient detail to enable those skilled in the art to practice the disclosure. It should be understood that the various embodiments of the present disclosure may be different but need not be mutually exclusive. For example, certain features, structures, and characteristics described herein may be implemented in other embodiments without departing from the spirit and scope of the disclosure in connection with one embodiment. Also, it should be understood that the locations or arrangements of the individual components of each disclosed embodiment may be varied without departing from the spirit and scope of the present disclosure. The following detailed description is, therefore, not provided for limitation, and the scope of the present disclosure is to be limited only by the appended claims and equivalents thereof, if properly explained. In the drawings, reference numerals refer to the same or similar functions throughout the several views.

Hereinafter, exemplary embodiments of the present disclosure will be described in detail with reference to the accompanying drawings.

Figure 2:
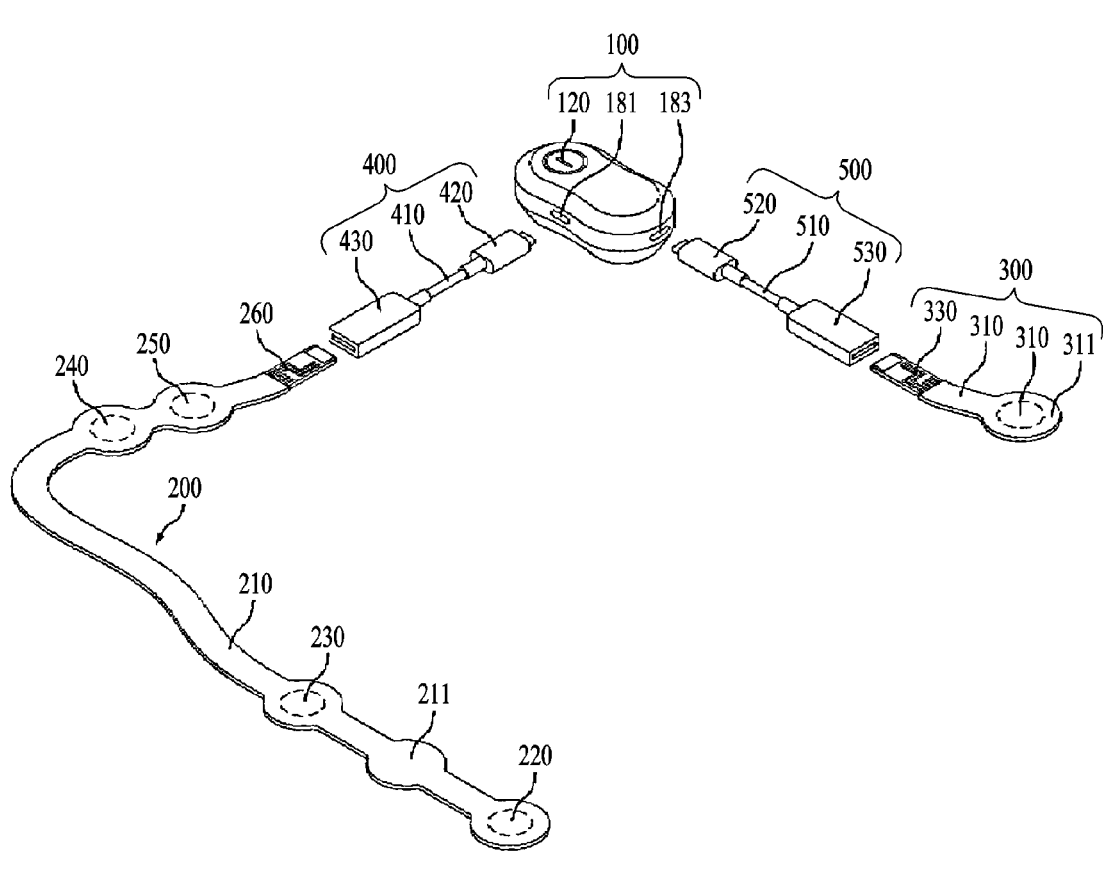
FIG. 2 illustrates constructions of the neurofeedback device according to an embodiment of the present disclosure.

FIG. 1 is a diagram for explaining a state in which a user wears a neurofeedback device according to an embodiment of the present disclosure, and FIG. 2 illustrates constructions of the neurofeedback device according to an embodiment of the present disclosure.

The neurofeedback device of the present disclosure measures or detects the user's brain waves, heart rate and movement by contacting a part of the user's body, and adjusts the intensity and frequency of electrodes for neurostimulation in real-time based on the measured or detected result to provide customized neurostimulation to the user.

The neurofeedback device according to the embodiment may be provided to include a body 100 for generating a neurofeedback signal for stimulation of the vagus nerve and outputting electrical stimulation, a brain wave measure 200, a genioglossus muscle stimulator 300, a first connection cable 400, and a second connection cable 500.

As shown in FIGS. 1 and 2, the body 100 may be provided to include a frame F, a vagus nerve stimulator 170, a heart rate sensor 130, a manipulator 120, and the plural connection ports 181 and 183.

First, the frame F is provided in an elliptical shape as shown in the drawing. Particularly, the frame F may be provided in a shape in which one side and the other side in a longitudinal direction are concave toward the center, thereby having a symmetrical structure.

In addition, the manipulator 120 for inputting a user's command may be located on a front surface of the frame F, and the vagus nerve stimulator 170 and heart rate sensor 130 for outputting electrical stimulation to stimulate the vagus nerve may be located on a back surface of the frame F.

In addition, the back surface of the frame F is provided such that electrical stimulation outputted from the vagus nerve stimulator 170 can be provided to a user's vagus nerve region, or is provided to be attachable the skin directly above the vagus nerve located next to the user's carotid artery, as shown in FIG. 1, to detect a user's heart rate.

For this, a part of the back surface of the frame(F), except for positions where the vagus nerve stimulator 170 and the heart rate sensor 130 are provided, may be provided with an adhesive member such as a gel pad to maintain the adhesive state to the wearer's skin, thereby preventing the body 100 from arbitrarily detaching from the user's skin.

In addition, the back surface of the frame F may be provided in a curved shape to be in contact with the user's neck, and to improve the adhesion of the frame F to a user's vagus nerve region compared to the case where only an adhesive member such as a gel pad is provided, a separate fixing member such as a strap may be further included.

Various modules and wires for generating electrical stimulation may be located inside the frame F.

Meanwhile, the vagus nerve stimulator 170 may be located on the back surface of the frame F and may be provided to include a first electrode 171 and second electrode 173 as a plurality of electrodes for outputting electrical stimulation, which corresponds to a neurofeedback signal, to a vagus nerve region.

The first electrode 171 and the second electrode 173 are respectively provided on the left and right of the frame F provided in a symmetrical structure, and, when the frame F is attached to the skin directly above the user's vagus nerve region, the frame F is arranged perpendicular to the direction of the vagus nerve as shown in FIG. 1, thereby providing electrical stimulation to the vagus nerve region. The first electrode 171 and the second electrode 173 may be provided as patch-type electrodes to be directly attached to the skin of the vagus nerve region.

Electrical stimulation corresponding to a neurofeedback signal for vagus nerve stimulation may be provided by the vagus nerve stimulator 170 including the first electrode 171 and the second electrode 173. In addition, the first electrode 171 and the second electrode 173 may be provided as circular electrodes as shown in the drawing.

Meanwhile, the heart rate sensor 130 may be located on the back surface of the frame F and located at the center of the left and right symmetry of the frame F provided in a symmetrical structure to detect a user's heart rate. That is, the heart rate sensor 130 is provided between the plural electrodes 171 and 173 as shown in FIG. 1.

Meanwhile, the manipulator 120 is located in front of the frame F to receive a user's command, and the power of the body 100 may be turned on/off by a user's operation.

In addition, the plural connection ports 181 and 183 may be provided to transmit and receive signals, and may be respectively formed on a side surface of the frame F as shown in FIG. 2. The first connection cable 400 or the second connection cable 500 is connected to the plural connection ports 181 and 183, and the body 100 may be connected to the brain wave measure 200 or the genioglossus muscle stimulator 300 through the first connection cable 400 or the second connection cable 500.

For this, as shown in the drawing, the plural connection ports 181 and 183 may be formed on one side of the frame F and the other side adjacent to the one side, and may be provided in a socket shape to allow insertion of a first terminal 420 of the first connection cable 400 or a second terminal 520 of the second connection cable 500.

Among the plural connection ports 181 and 183, the connection port 181 on one side of the frame F to be connected to the first connection cable 400 may be formed at a concavely recessed portion of the frame F formed symmetrically from left to right as shown in FIG. 2. Due to the position of the connection port 181 on one side of the frame F, the plural electrodes 171 and 173 of the vagus nerve stimulator 170 may be arranged perpendicular to the direction of the vagus nerve when the brain wave measure 200 connected to the body 100 through the first connection cable 400 is attached to a portion of the user's head through the periphery of the user's ear and, at the same time, the frame (F) is attached to the skin directly above the user's vagus nerve region.

In addition, among the plural connection ports 181 and 183, the connection port 183 formed on the other side adjacent to one side connected to the second connection cable 500 may be formed on the other side that is one end in a longitudinal direction of the frame F formed symmetrically from left to right, not the concavely recessed portion of the frame F, as shown in FIG. 2. Due to the position of the connection port 183 formed on the other side adjacent to one side, a genioglossus muscle electrode 320 of the genioglossus muscle stimulator 300 connected to the body 100 through the second connection cable 500 may be attached to the skin of the user's genioglossus muscle region.

Through the body 100, the neurofeedback device according to the embodiment may provide electrical stimulation corresponding to a neurofeedback signal to the vagus nerve region.

In addition, the body 100 may be provided to further include an inertial sensor as a motion sensor 140 for detecting a user's motion.

Meanwhile, the brain wave measure 200 is attached to the user's head to measure the user's brain waves. The brain waves measured by the brain wave measure 200 may be transmitted to a controller provided in the body 100 to utilize as data for generating a neurofeedback signal.

The brain wave measure 200 may be connected to the body 100 through the first connection cable 400, may transmit and receive signals to and from the body 100 through the first connection cable 400, and may be provided to include a first band 210, a first brain wave sensor 220, a second brain wave sensor 230, a reference electrode 240, a ground electrode 250, and a first connector 260.

First, the first band 210 is provided to be attached to the user in a form of extending and being attached over a part of the head past the back of the user's ear from around the user's neck in a state in which the brain wave measure 200 is partially connected to the body 100. As shown in the drawing, the first band 210 may be provided in a band shape having a predetermined width, and may be provided in a material that can be changed in response to the curvature of the human body so as to be in contact with the user's head. Here, the predetermined width means a width on which the first brain wave sensor 220, the second brain wave sensor 230, the reference electrode 240, and the ground electrode 250 can be arranged, and may be provided to be greater than or equal to the diameters of the first brain wave sensor 220, the second brain wave sensor 230, the reference electrode 240, and the ground electrode 250.

As shown in FIG. 1, when, in the brain wave measure 200 connected to the body 100, a portion furthest from the body 100 is assumed as one end of the first band 210, the first brain wave sensor 220, the second brain wave sensor 230, the reference electrode 240, and the ground electrode 250 are arranged on a back surface of the first band 210 in order from the one end of the first band 210 to the other end close to the body 100, and the other end of the first band 210 is provided with the first connector 260 to be coupled with the first connection cable 400.

In addition, parts, on which the first brain wave sensor 220, the second brain wave sensor 230, the reference electrode 240 and the ground electrode 250 are to be arranged, of the first band 210 are provided in a circular shape having a larger diameter than the predetermined width, wherein the circular shape has a larger diameter than the first brain wave sensor 220, second brain wave sensor 230, reference electrode 240, and ground electrode 250 provided in a circular shape, as shown in the drawing. Thereby, the first brain wave sensor 220, the second brain wave sensor 230, the reference electrode 240 and the ground electrode 250 may be stably fixed, and an area of the brain wave measure 200 in close contact with the user's skin may be widened, thereby improving adhesion.

In particular, a circular shape having a larger diameter than the predetermined width may also be provided between the first brain wave sensor 220 and the second brain wave sensor 230 as shown in FIG. 2, and an adhesive member such as a gel pad may be attached to a back surface of the circular shape, thereby preventing the brain wave measure 200 from arbitrarily detaching from the user's head.

Meanwhile, the first brain wave sensor 220 may be located on a back surface of one end of the first band 210 and may be provided in the form of a patch to be detachably attached to a part of the user's head. The first brain wave sensor 220 is provided to measure brain waves in the left prefrontal lobe Fp1 region of the user.

Meanwhile, the second brain wave sensor 230 may be located at a rear end of the first brain wave sensor 220 on the back surface of the first band 210, and may be provided in the form of a patch, as in the first brain wave sensor 220 so as to be detachably attached to a part of the user's head. In addition, the second brain wave sensor 230 may measure brain waves in the right prefrontal lobe Fp2 region of the user.

In addition, brain wave signals measured by the first brain wave sensor 220 and the second brain wave sensor 230 may be transmitted to the body 100 through the first connector 260.

Meanwhile, the reference electrode 240 is located at a rear end of the second brain wave sensor 230 on the back surface of the first band 210 and is provided to be detachably attached around the user's ear so as to provide a reference signal for brain wave measurement.

In addition, the ground electrode 250 is located at a rear end of the reference electrode 240 on the back surface of the first band 210 and is provided to be detachably attached around the user's ear so as to provide a ground signal for brain wave measurement.

In the neurofeedback device according to the embodiment, the reference electrode 240 and the ground electrode 250 are arranged together on the first band 210 so that there is no need to additionally provide a separate means for providing a reference signal and a ground signal.

Meanwhile, the first connector 260 is provided to connect the brain wave measure 200 to the body 100 through the first connection cable 400, is located at the other end of the first band 210 which is a rear end of the ground electrode 250, and is inserted into a first socket 430 of the first connection cable 400 to be coupled to the first connection cable 400.

Accordingly, the brain wave measure 200 may transmit the measured brain wave signals, the reference signal, and the ground signal to the body 100 through the coupling between the first connector 260 and the first connection cable 400.

Meanwhile, the genioglossus muscle stimulator 300 is attached around the user's neck and is provided to output electrical stimulation corresponding to a neurofeedback signal. The genioglossus muscle stimulator 300 may be connected to the body 100 through the second connection cable 500 and may be provided to include a second band 310, a genioglossus muscle electrode 320, and a second connector 330.

First, the second band 310 may be provided to fix the genioglossus muscle electrode 320 and to attach the genioglossus muscle electrode 320 to the user's genioglossus muscle region, and may be provided in a band shape having a predetermined width as shown in the drawing. Here, the predetermined width means a width on which the genioglossus muscle electrode 320 can be arranged, and may be at least equal to or greater than the diameter of the genioglossus muscle electrode 320.

In addition, a back surface of the second band 310 may be provided to include an adhesive member such as a gel pad such that the genioglossus muscle stimulator 300 including the genioglossus muscle electrode 320 can be attached around the user's neck or chin. The second band is preferably attached to a region including the skin directly above the genioglossus muscle region of the user's skin.

In addition, as in the first band 210, a part, on which the genioglossus muscle electrode 320 is to be arranged, of the second band 310 is formed in a circular shape with a larger diameter than the predetermined width, thereby improving the adhesion of the genioglossus muscle stimulator 300 to the user's skin.

In addition, the genioglossus muscle electrode 320 may be located on a back surface of one end of the second band 310, the second connector 330 may be located at the other end of the second band 310, and the second band 310 has preferably a length enabling the genioglossus muscle electrode 320 to reach the genioglossus muscle region so as to provide electrical stimulation to the user's genioglossus muscle in a state of being connected to the body 100 through the second connection cable 500.

Meanwhile, the genioglossus muscle electrode 320 may be provided in the user's genioglossus muscle region to output electrical stimulation corresponding to a neurofeedback signal, and may be located on a back surface of one end of the second band 310, and may be provided in the form of a patch to be attached to the skin directly above the user's genioglossus muscle region.

In addition, the second connector 330 is provided to connect the genioglossus muscle stimulator 300 to the body 100 through the second connection cable 500. The second connector 330 may be located at the other end of the second band 310 and inserted into a hole of a second socket 530 of the second connection cable 500 to be connected to the second connection cable 500.

Accordingly, the genioglossus muscle stimulator 300 may output electrical stimulation corresponding to a neurofeedback signal through the genioglossus muscle electrode 320 to provide the outputted electrical stimulation to the user.

Meanwhile, the first connection cable 400 may be provided to connect the body 100 and the brain wave measure 200 to each other to transmit and receive signals between each other, and may be provided to include a first cable 410, the first terminal 420, and the first socket 430.

The first cable 410 may be made of a conductive material so that the body 100 and the brain wave measure 200 can transmit and receive signals between each other. One end of the first cable 410 may be connected to the first terminal 420 and the other end thereof may be connected to the first socket 430.

The first terminal 420 may be provided to connect the first connection cable 400 and the body 100 to each other and may be located at one end of the first cable 410.

In addition, the first terminal 420 may be fitted into the one connection port 181 among the plural connection ports 181 and 183 of the body 100, thereby being connected to the body 100. As shown in the drawing, the first terminal 420 may be provided with a protruding terminal to be inserted into the connection port 181, thereby being connected to the body 100.

The first socket 430 may be provided to connect the first connection cable 400 to the brain wave measure 200. The first socket 430 is located at the other end of the first cable 410, and is provided with a hole therein to allow insertion of the first connector 260 of the brain wave measure 200 thereinto to be connected to the brain wave measure 200.

Through the first connection cable 400, the body 100 of the neurofeedback device may be connected to the brain wave measure 200 and may transmit and receive signals with the brain wave measure 200 through the first connection cable 400.

Meanwhile, the second connection cable 500 may be provided to connect the body 100 and the genioglossus muscle stimulator 300 to each other to transmit and receive signals between each other, and may be provided to include a second cable 510, the second terminal 520, and the second socket 530.

The second cable 510 may be made of a conductive material so that the body 100 and the genioglossus muscle stimulator 300 can transmit and receive signals between each other. One end of the second cable 510 may be connected to the second terminal 520, and the other end thereof may be connected to the second socket 530.

The second terminal 520 may be provided to connect the second connection cable 500 to the body 100, and may be located at one end of the second cable 510.

In addition, the second terminal 520 may be fitted into the other connection port 183 of the plural connection ports 181 and 183 of the body 100, thereby being connected to the body 100. As shown in the drawing, the second terminal 520 may be provided with a protruding terminal to be inserted into the other connection port 183 as in the first terminal 420, thereby being connected to the body 100.

The second socket 530 may be provided to connect the second connection cable 500 to the genioglossus muscle stimulator 300. The second socket 530 may be located at the other end of the second cable 510 and the second connector 330 of the genioglossus muscle stimulator 300 may be inserted thereinto, thereby being connected to the genioglossus muscle stimulator 300. In addition, the second socket 530 is provided with a hole therein such that the second connector 330 can be inserted thereinto.

Through the second connection cable 500, the body 100 of the neurofeedback device may be connected to the genioglossus muscle stimulator 300 and may transmit and receive various signals with the genioglossus muscle stimulator 300.

Due to such a configuration, the user may receive vagus nerve stimulation only using the body 100, and the brain wave measure 200, first connection cable 400, genioglossus muscle stimulator 300, and second connection cable 500 configured to be detachably attached to the body 100 may be selectively connected.

Accordingly, in the case of the neurofeedback device according to the embodiment, the body 100 may be connected to any one of the brain wave measure 200 and the genioglossus muscle stimulator 300 or may be simultaneously connected to the brain wave measure 200 and the genioglossus muscle stimulator 300 according to the user's need.

Figure 3:
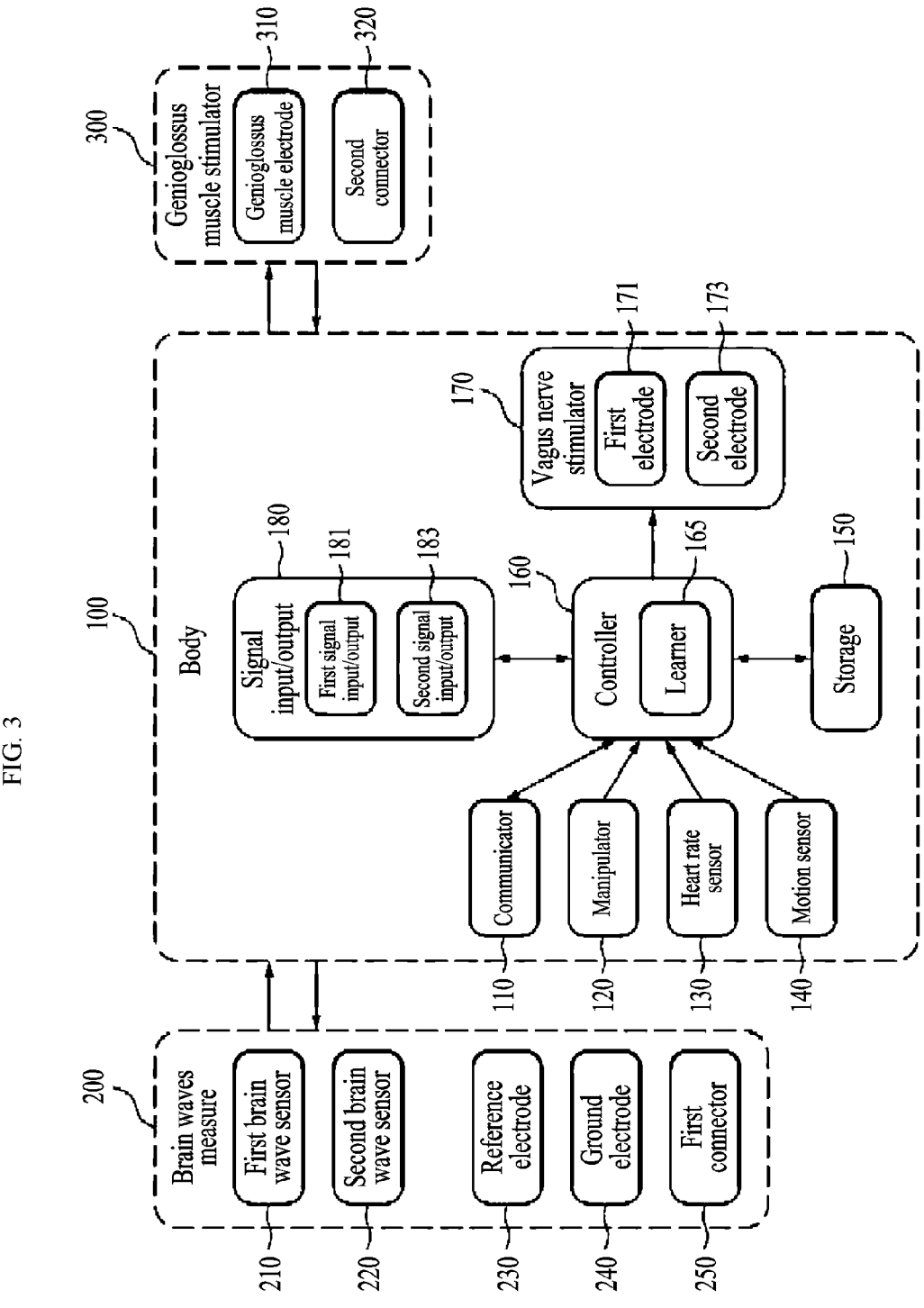
FIG. 3 is a block diagram for explaining the configuration of a neurofeedback system according to an embodiment of the present disclosure.

FIG. 3 is a block diagram for explaining the configuration of a neurofeedback system according to an embodiment of the present disclosure.

As described above with reference to FIGS. 1 and 2, a neurofeedback system including the neurofeedback device of the present disclosure may be provided to include the body 100, the brain wave measure 200, the genioglossus muscle stimulator 300, the first connection cable 400, and the second connection cable 500. Here, the body 100 may be installed and executed with software (application) for performing neurofeedback control. In addition, all the components included in the body 100 and the components of the brain wave measure 200 and the genioglossus muscle stimulator 300 may be controlled by software for performing neurofeedback control executed by the neurofeedback device.

First, the body 100 receives and analyzes data corresponding to a biosignal measured or detected from the user's body to generate a neurofeedback signal, provides electrical stimulation to a preset area of the user's body according to the generated neurofeedback signal, and is provided to be attached to a part of the user's body.

For this, the body 100 may include a communicator 110, a manipulator 120, a heart rate sensor 130, a motion sensor 140, a storage 150, a controller 160, a vagus nerve stimulator 170, and a signal input/output 180. Such components may be controlled by software for performing neurofeedback control executed in the main body 100, and the components constituting the main body 100 may be formed of an integrated module, or may consist of one or more modules. Conversely, it is possible that each component may be formed of a separate module.

First, the communicator 110 is provided to transmit and receive necessary information from an external device or an external network, and thus may receive learning data or software for neurofeedback control.

The manipulator 120 is provided as an input means for receiving a user command as described above, and is provided as a button outside the frame F constituting the body 100 to receive a command through pressure by the user. The power of the body 100 may be set to turn on or off depending upon a time where the manipulator 120 is pressurized. In addition, the mode of the body 100 may change depending upon the number of times the manipulator 120 is pressed for a certain time.

Meanwhile, the heart rate sensor 130 is provided to measure the user's heart rate, and is located on the back of the body 100 to measure the heart rate around the user's neck. The heart rate measured by the heart rate sensor 130 is heart rate data and may be transmitted to the control unit 160. The heart rate sensor 130 may be provided as a photoplethysmographic wave (PPG) sensor, and may be provided on the back surface of the frame F of the body 100 to be in contact with the user's body.

In addition, the heart rate sensor 130 may continuously detect a photoplethysmographic wave signal that is the user's heart rate for electrical stimulation corresponding to a neurofeedback signal provided by the vagus nerve stimulator 170 or the genioglossus muscle stimulator 300, and may continuously transmit the detected heart rate data to the controller 160.

The motion sensor 140 is provided to detect a user's motion and may be provided inside the frame F of the body 100, and the motion sensor 140 according to the present embodiment may be provided as an inertial sensor. Through the motion sensor 140, it is possible to detect the movement of the user during sleep. In addition, the user's motion detected by the motion sensor 140 may be transmitted to the controller 160 as motion data.

Like the heart rate sensor 130, the motion sensor 140 may continuously detect a user's motion for electrical stimulation corresponding to a neurofeedback signal provided by the vagus nerve stimulator 170 or the genioglossus muscle stimulator 300, and may continuously transmit the detected motion data to controller 160.

Meanwhile, the storage 150 may record a program for performing neurofeedback control, may provide the storage space necessary for the controller 160 to operate, may temporarily or permanently store the data processed by the controller 160, and may include a volatile storage medium or a non-volatile storage medium, but the scope of the present disclosure is not limited thereto.

In addition, the storage 150 may store data accumulated while performing a neurofeedback control. In addition, a custom neurofeedback model for a user may be pre-built and pre-stored in the storage 150.

Meanwhile, the controller 160 may analyze the measured brain wave data, the measured heart rate data, and the detected motion data, may generate a neurofeedback signal for electrical stimulation, and may cause electrical stimulation corresponding to the generated neurofeedback signal to be output through the vagus nerve stimulator 170 and the genioglossus muscle stimulator 300.

In addition, the controller 160 may analyze the continuously detected brain wave data, heart rate data, and motion data to generate a user's current clinical indicator and may generate a neurofeedback signal corresponding to the generated current clinical indicator.

In addition, when a neurofeedback device is worn by the user and turned on, the controller 160 may use the strength of the signal included in the data received from the brain wave measure 200, the heart rate sensor 130 and the motion sensor 140 as a response to determine whether the neurofeedback device is normally attached to a part of the user's body.

Specifically, when the strength of the signal included in the brain wave data, heart rate data, and motion data is less than a certain strength, it is determined that a change in the attached area is necessary, and a related signal is output to guide the user. When it is determined that reactivity is higher than or equal to a preset reactivity, the brain wave measure 200, the heart rate sensor 130, and the motion sensor 140 may continuously detect brain wave data, heart rate data, and motion data.

In addition, a mode of the neurofeedback device of the present disclosure may be changed according to the manipulation of the manipulator 120. A mode in the present disclosure may include a measure mode and a stimulation mode.

The measure mode may be a mode wherein brain wave signals, heart rate signals, and motion signals through the brain wave measure 200, the heart rate sensor 130, and the motion sensor 140 are only measured, and brain wave data, heart rate data, and motion data are stored in the storage 150, But it may generate a separate neurofeedback signal and not generate a corresponding electrical stimulation.

This mode may be a mode that is set when the pressure of the manipulator 120 is detected twice for a preset time through the manipulator 120 after the neurofeedback device is powered on by the manipulation of the manipulator 120, and the preset time is 1 to 2 seconds. That is, when the manipulator 120 is pressurized twice or more within 2 seconds, the controller 160 may change to a measure mode to collect data only for various signals, store the collected data in the storage 150, and control so that a separate neurofeedback signal is not generated.

Meanwhile, the stimulation mode is a mode that analyzes measured brain wave data, heart rate data, and motion data and generated a neurofeedback signal based on the analyzed data when pressure through the manipulator (120) is not detected after the neurofeedback device is powered on.

Accordingly, although not shown in the drawings, the body 100 of the present disclosure may further include a separate output (not shown), such as a speaker or a display, for informing the user of a change in the attachment position or a mode state, and the controller 160 may cause a voice or image to guide a change of the attachment position or guide the stimulation mode or the measurement mode to be outputted through the output (not shown). For this, the voice or image outputted from the output (not shown) may be previously stored in the storage 150.

To generate a neurofeedback signal by the controller 160, the controller 160 according to the present embodiment may be provided to include a machine learning-based learner 165 to construct a neurofeedback algorithm for generating a neurofeedback signal.

The neurostimulation-providing neurofeedback algorithm is a machine learning-based neurofeedback model and, to provide electrical stimulation to improve a user's sleep disorder, it is necessary to measure the user's brain wave signals to classify the user's individual sleep stages. In this process, learning of the neurofeedback model is carried out based on data measured when a user's brain signal is measured in advance or when the neurofeedback device is used for the first time. To construct a customized neurofeedback model, autonomic nervous system activation information and user characteristics-dependent sleep stages are classified based on the brain wave signals, heart rate signals, and motion signals measured according to user characteristics. In addition, brain wave signals, heart rate signals, motion signals, and clinical indicators obtained by analyzing the signals may be converted into input variables of the machine learning algorithm, and then user's sleep stages may be classified, and neurofeedback signals corresponding to appropriate nerve stimulation in the classified sleep stages may be generated.

The clinical indicator may be at least one of the following: power spectra density based on brain wave data, heart rate variability based on heart rate data, and degree of motion based on motion signals.

Therefore, the controller 160 analyzes brain wave data, heart rate data, and movement data detected from a sleeping device-user according to the neurofeedback algorithm to calculate autonomic nervous system activation information and real-time sleep stage classification result. Through this, it is possible to generate personalized vagus nerve stimulation and genioglossus muscle stimulation optimized for the user from the generated user's current clinical indicators. Here, appropriate vagus nerve stimulation and genioglossus muscle stimulation may be stimulations to reach the target state of parasympathetic activation set by a user by utilizing a power spectrum density using brain wave data among the detected data and a heart rate variation index using heart rate data.

Since activation of the parasympathetic nerve through vagus nerve stimulation during sleep increases the size of the low-frequency and alpha bands of brain waves, thereby promoting the plasticity of the synapse and increasing cognitive function, the controller 160 may determine the degree of activation of the wearer's parasympathetic nerve in real-time by utilizing the continuously detected brain wave data and heart rate data.

Accordingly, the controller 160 may continuously generate a neurofeedback signal for user-customized electrical stimulation calculated according to the neurofeedback algorithm in real-time and may transmit the generated neurofeedback signal to the vagus nerve stimulator 170 and the genioglossus muscle stimulator 300, thereby providing vagus nerve and genioglossus muscle stimulation suitable for the user in real-time.

Meanwhile, the vagus nerve stimulator 170 may be provided to stimulate the vagus nerve within a preset area including the vagus nerve of the user, located on a back surface of the frame F of the body 100, and provided in the form of a patch to be detachably attached to the user's body.

In addition, the vagus nerve stimulator 170 is provided to include the first electrode 171 and the second electrode 173 so as to output electrical stimulation corresponding to the neurofeedback signal received from the controller 160.

The first electrode 171 and the second electrode 173 may output a current of intensity and frequency corresponding to the neurofeedback signal received from the controller 160, thus providing electrical stimulation to the user's vagus nerve region to which the first electrode 171 and the second electrode 173 are attached.

Vagus nerve stimulation via the first electrode 171 and the second electrode 173 stimulates Locus Coeruleus (LC) via Nucleus Tractus Solitarius (NTS), and LC stimulates dorsal raphe Nucleus (DRN) by stimulating norepinephrine (NE) secretion, thereby increasing serotonin (5-HT) secretion and melatonin. As a result, sleep disorders caused by melatonin deficiency can be improved.

Therefore, the vagus nerve stimulator 170 stimulates the vagus nerve connected to the central nervous system to help autonomic nerve function and activation of the brain neural network, thereby promoting synaptic plasticity in the cerebral cortex and hippocampus, which controls cognitive function, to improve the user's cognitive function.

When the first electrode 171 and the second electrode 173 provide electrical stimulation corresponding to a neurofeedback signal, electrical stimulation may be simultaneously outputted from the first electrode 171 and the second electrode 173 or from one of the first electrode 171 and the second electrode 173.

The signal input/output 180 may be provided such that the main body 100 transmits/receives various signals to and from at least one of the brain wave measure 200 and the genioglossus muscle stimulator 300, and may include a first signal input/output 181 and a second signal input/output 183.

The first signal input/output 181may be connected to the first connection cable 400 for connecting the main body 100 and the brain wave measure 200 to each other to transmit and receive various signals to and from the brain wave measure 200 and transmit the signals to the control unit 160.

The second signal input/output 183 may be connected to the second connection cable 500 for connecting the body 100 and the genioglossus muscle stimulator 300 to each other to transmit and receive various signals to and from the genioglossus muscle stimulator 300 and transmit the signals to the control unit 160.

Figure 4:
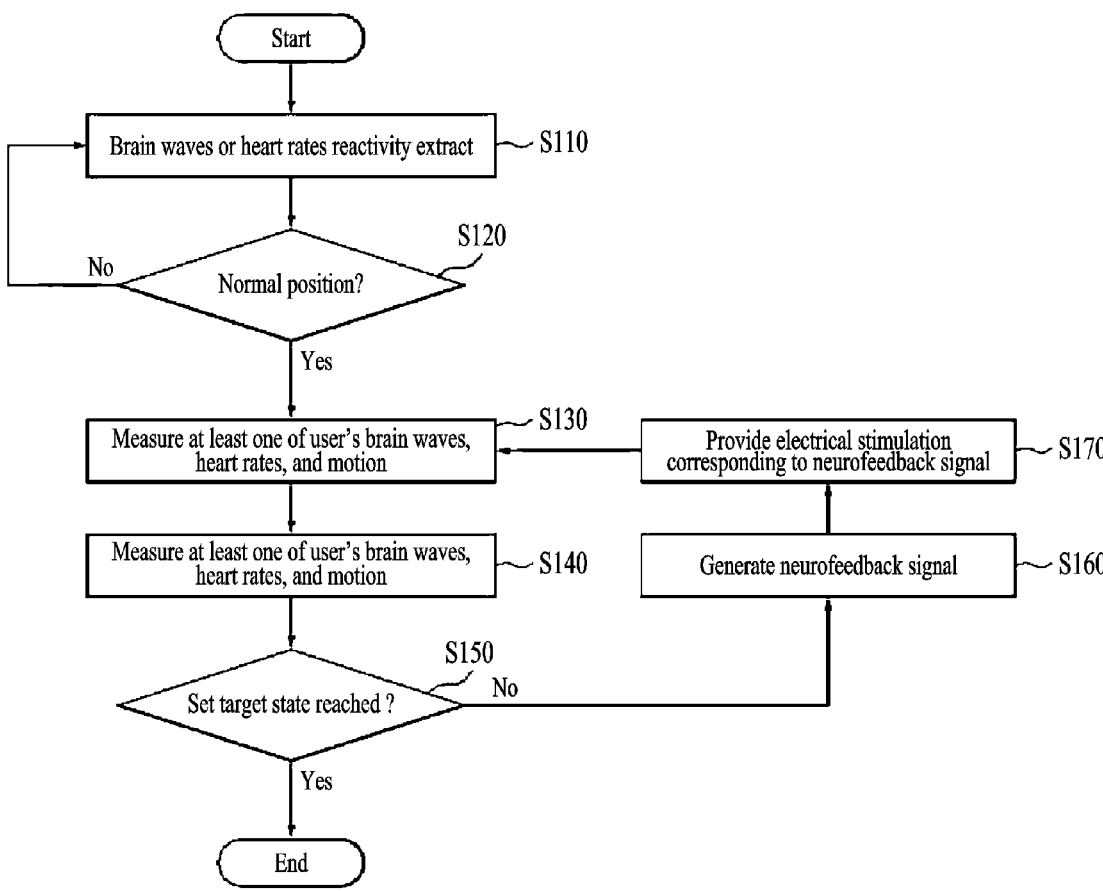
FIG. 4 is a flowchart for explaining a neurofeedback control method according to an embodiment of the present disclosure.

In FIGS. 3 and 4, the first signal input/output 181 and second signal input/output 183 included in the signal input/output 180 are the same as the plural connection ports 181 and 183. However, for convenience of explanation, the connection ports 181 and 183 are described in FIGS. 1 and 2, and the signal input/output 180 including the first signal input/output 181 and second signal input/output 183 for performing signal transmission/reception with the controller 160 is described in FIGS. 3 and 4.

Meanwhile, the brain wave measure 200 may be provided to measure the brain waves of the sleeping user and transmit the measured brain waves signal to the main body 100 as brain waves data, and may be provided to include the first brain wave sensor 220, the second brain wave sensor 230, the reference electrode 240, the ground electrode 250, and the first connector 260.

The first brain wave sensor 220 may be provided in the form of a patch, may be detachably attached to a part of the user's head, and may measure a first brain wave signal in the user's left prefrontal lobe (Fp1) region.

Meanwhile, the second brain wave sensor 230 may be provided in the form of a patch like the first brain wave sensor 220, may be provided to be detachably attached to a part of the user's head, and may measure a second brain wave signal in the user's right prefrontal lobe (Fp2) region.

The first brain wave sensor 220 and the second brain wave sensor 230 may continuously detect user's brain wave data for electrical stimulation corresponding to the neurofeedback signal provided by the vagus nerve stimulator 170 and may transmit the detected data to the main body 100.

Meanwhile, the reference electrode 240 and the ground electrode 250 may be included to provide a reference signal and a ground signal for measuring brain wave signals in the first brain wave sensor 220 and the second brain wave sensor 230.

The brain wave measure 200 of the present disclosure may include the reference electrode 240 and the ground electrode 250 to obtain a ground signal and a reference signal in the user's ear region.

Therefore, there is no need to additionally provide a separate means for providing a reference signal and a ground signal, and the accuracy of brain wave signals to be measured may be improved through impedance matching between the first brain wave sensor 220 and the second brain wave sensor 230 and between the reference electrode 240 and the ground electrode 250.

The contact area of the reference electrode 240 and the ground electrode 250 in contact with the user is preferably provided in the same size as the contact area of the first brain wave sensor 220 and the second brain wave sensor 230 in contact with the user, but the size may be changed in consideration of impedance matching.

In addition, the first connector 260 may be provided to connect the brain wave measure 200 to the body 100 and may be connected to the first socket 430 located at the other end of the first connection cable 400 for connecting the body 100 to the brain wave measure 200 as shown in FIG. 2, thereby transmitting and receiving various signals to and from the body 100.

Meanwhile, the genioglossus muscle stimulator 300 may output electrical stimulation corresponding to a neurofeedback signal received from the body 100 to provide electrical stimulation to a preset area including the user's genioglossus muscle.

For this, the genioglossus muscle stimulator 300 may provide electrical stimulation by outputting a current having an intensity and a frequency corresponding to a neurofeedback signal in a preset region including the user's genioglossus muscle.

For this, the genioglossus muscle stimulator 300may be provided to include the genioglossus muscle electrode 320 and the second connector 330. The genioglossus muscle electrode 320 is provided to output a current having an intensity and a frequency corresponding to a neurofeedback signal.

The neurofeedback device of the present disclosure may provide electrical stimulation for simulating the percutaneous nerves around the user's genioglossus muscle through the genioglossus muscle stimulator 300, thereby causing the tongue to move in the forward direction. Accordingly, an upper airway may be secured, and effective prevention and response to sleep apnea patients whose symptoms of obstructive sleep apnea are caused by relaxation of muscles, etc. may be made.

In addition, the first electrode 171, the second electrode 173, the first brain wave sensor 220, the second brain wave sensor 230, the reference electrode 240, the ground electrode 250, and the genioglossus muscle electrode 320 described above may be electrode patches, may have a circular sheet shape, and may be made of a deformable material, but are not limited to a circular sheet and may be a rectangular sheet or other shape sheets. In addition, the respective electrodes 171, 173, 240, 250, and 320, and the respective sensors 220 and 230 are located on the back surface of the frame F of the body 100, a conductive terminal is located in the center of one surface in contact with the first band 210 and the second band 310, and the other surface is applied with a hydrogel layer to cover the conductive terminal so that the terminal is fixed to the back surface of the frame F of the body 100, the first band 210, and the second band 310 and the hydrogel layer is in contact with the user's skin.

The second connector 330 may be provided to connect the genioglossus muscle stimulator 300 to the body 100 and, as shown in FIG. 2, may be inserted into and connected to the second socket 530 of the second connection cable 500 for connecting the body 100 and the genioglossus muscle stimulator 300, thereby transmitting/receiving various signals to and from the body 100.

Although not shown in FIG. 3, the first connection cable 400 may transmit a signal transmitted/received between the body 100 and the brain wave measure 200 by connecting the body 100 and the brain wave measure 200 to each other, and the second connection cable 500 may transmit a signal transmitted/received between the body 100 and the genioglossus muscle stimulator 300 by connecting the body 100 and the genioglossus muscle stimulator 300 to each other, as described in FIGS. 1 and 2. Accordingly, the body 100 and the brain wave measure 200 or the body 100 and the genioglossus muscle stimulator 300 may interwork.

Unlike a conventional neurofeedback device that provides only electrical stimulation of a preset specific frequency (Hz) and intensity (mA), the neurofeedback device and neurofeedback system including the constructions as described above may measure and detect brain waves, heart rate, and motion, and may evaluate a user's condition based on the measured brain waves, heart rate, and motion, in real-time, and may generate an appropriate neurostimulation neurofeedback signal based on the evaluated results, thereby providing optimized vagus nerve stimulation and genioglossus muscle stimulation to the user in real-time. Thereby, symptoms of various diseases such as sleep disorders, anxiety disorders, and cognitive dysfunction may be improved.

Meanwhile, FIG. 4 is a flowchart for explaining a neurofeedback control method according to an embodiment of the present disclosure. In the neurofeedback control method performed by the above-described neurofeedback system, first, the neurofeedback device may be attached to the user's body so as to be located within a preset area.

In this step, the neurofeedback device is attached to the user's body such that the body 100 is located in a preset area including the vagus nerve, the brain wave measure 200 is located at a left prefrontal lobe region and a right prefrontal lobe region, and the genioglossus muscle stimulator 300 is located at a preset area including the genioglossus muscle. The genioglossus muscle stimulator 300 may be omitted without being attached to the user, as needed.

When the neurofeedback device is attached to the user, the controller 160 extracts the reactivity of the measured brain wave data and heart rate data from the brain wave measure 200 and the heart rate sensor 130 (S110). The reactivity may be extracted based on the intensity of the collected brain wave signals and heart rate signals.

The controller 160 determines whether the neurofeedback device is located at a normal position (S120). This is determined based on the extracted reactivity, and the measured intensity of each signal is used as a reactivity and is compared with a pre-set reactivity.

When the reactivity is less than the preset reactivity, it is determined that the neurofeedback device is not in the normal position (S120—No), and the process may return to a step of extracting the reactivity (S110). Although not shown in the drawing, at this time, a signal guiding the user that a location change is required may be generated and outputted.

On the other hand, when the reactivity extracted from the intensity of each signal is greater than or equal to the preset reactivity, it is determined that the neurofeedback device is in the normal position (S120—Yes).

Then, the neurofeedback device performs a measurement step of measuring at least one of the user's brain waves, heart rates, and motion (S130).

The heart rate sensor 130 of the body 100 may measure the user's heart rate signal to transmit heart rate data to the controller 160, the motion sensor 140 may detect the user's motion signal to transmit motion data to the controller 160, and the brain wave measure 200 may measure the user's brain wave signal to transmit brain wave data to the controller 160.

Next, the controller 160 may analyze at least one of the brain wave data, heart rate data and motion data measured in the measurement step S130 to generate a clinical indicator (S140).

Specifically, the controller 160 may calculate autonomic nervous system activation information and real-time sleep stage classification results by analyzing the brain wave data, heart rate data and motion data detected from the sleeping wearer according to the neurofeedback algorithm.

Then, the controller 160 may determine based on the generated clinical indicator whether a set target state has been reached (S150).

The controller 160 may calculate autonomic nervous system activation information and real-time sleep stage classification results by analyzing the brain wave data, heart rate data and motion data detected from the sleeping user according to the neurofeedback algorithm, may determine whether a parasympathetic activation target state has been reached by comparing the generated user's current clinical indicator with a set parasympathetic activation target state. When it is determined that a current clinical indicator has reached the set parasympathetic activation target state (S150—Yes), the execution of the neurofeedback control method may be terminated.

On the other hand, when it is determined that the current clinical indicator has not reached the set parasympathetic activation target state (S150—No), the controller 160 may generate a neurofeedback signal corresponding to the clinical indicator (S160).

The controller 160 may classify a user's sleep stage through the neurofeedback algorithm using brain wave data, heart rate data, motion data, and a clinical indicator and may generate a neurofeedback signal corresponding to appropriate neurostimulation in the classified sleep stage.

Specifically, the controller 160 may generate personalized vagus nerve stimulation and genioglossus muscle stimulation optimized for the user from a user's current clinical indicator generated through the step S140 of calculating autonomic nervous system activation information and real-time sleep stage classification results by analyzing the brain wave data, heart rate data and motion data detected from the sleeping wearer according to the neurofeedback algorithm. Here, the appropriate vagus nerve stimulation and genioglossus muscle stimulation may be stimulation to reach a parasympathetic activation target state that has been set by the user by utilizing a power spectrum density, which uses the brain wave data among the detected data, and a heart rate variability index which uses the heart rate data.

Activation of the parasympathetic nerve through vagus nerve stimulation during sleep increases the size of the low-frequency and alpha bands of the brain waves, thereby promoting the plasticity of the synapse and increasing the cognitive function. Accordingly, the controller 160 may determine the degree of activation of the wearer's parasympathetic nerve in real-time by utilizing the continuously detected brain wave data and heart rate data.

Accordingly, the controller 160 may continuously generate a neurofeedback signal for user-customized electrical stimulation, calculated according to the neurofeedback algorithm, in real-time.

Next, the neurofeedback device may provide electrical stimulation corresponding to the neurofeedback signal (S170).

The step S170 of providing electrical stimulation may include at least one of a vagus nerve stimulation step in which the vagus nerve stimulator 170 outputs electrical stimulation corresponding to a neurofeedback signal to provide into the preset region including the vagus nerve; and a genioglossus muscle stimulation step in which the genioglossus muscle stimulator 300 outputs electrical stimulation corresponding to a neurofeedback signal to provide into a preset area including the genioglossus muscle.

After the step (S170) of providing electrical stimulation, it may return to the measurement step S130 of measuring at least one of the user's brain waves, heart rates, and motion, and brain waves, heart rates, and motion may be continuously measured while the user is sleeping to generate a neurofeedback signal according to the analysis result.

Therefore, by the neurofeedback control method of the present disclosure, the user can be provided with personalized vagus nerve stimulation and genioglossus muscle stimulation optimized for him/her, thereby improving sleep disorders and further preventing deterioration of cognitive function. In addition, effective prevention and response to sleep apnea patients can be provided.

The neurofeedback control method of the present disclosure can include a computer readable medium including program commands for executing operations implemented through various computers. The computer readable medium can store program commands, data files, data structures or combinations thereof.

The program commands recorded in the computer readable medium may be specially designed and configured for the present disclosure or be known to those skilled in the field of computer software.

Examples of a computer readable recording medium include magnetic media such as hard disks, floppy disks and magnetic tapes, optical media such as CD-ROMs and DVDs, magneto-optical media such as floptical disks, or hardware devices such as ROMs, RAMs and flash memories, which are specially configured to store and execute program commands.

Examples of the program commands include a machine language code created by a compiler and a high-level language code executable by a computer using an interpreter and the like.

The hardware devices may be configured to operate as one or more software modules to perform operations in the embodiments, and vice versa.

In accordance with an aspect of the present disclosure, by providing a neurostimulation-based neurofeedback device using brain waves and heartbeat signals and a method thereof, optimized personalized vagus nerve stimulation based on autonomic nervous system activation information and real-time sleep stage classification results collected through brain waves and heart rate signals measured during sleep can be provided.

In addition, by providing the optimized personalized vagus nerve stimulation, sleep disorders can be improved and deterioration of cognitive function can be prevented.

Further, by providing personalized vagus nerve stimulation through a solution of providing both monitoring and nerve stimulation, symptoms of various diseases such as sleep disorders, anxiety disorders, and cognitive dysfunction can be improved.

As described above, various embodiments of the present disclosure have been illustrated and described, but the present disclosure is not limited to the specific embodiments described above. Various modifications may be made by those with ordinary knowledge in the technical field to which the disclosure belongs without departing from the gist of the present disclosure claimed in the claims, and these modifications should not be understood individually from the technical spirit or perspective of the present disclosure.

DESCRIPTION OF SYMBOLS

100: body 200: brain wave measure
300: genioglossus muscle stimulator 400: first connection cable
500: second connection cable

What is claimed is:
1. A neurofeedback device comprising:
a body configured to be attached to a user's skin and configured to provide electrical stimulation to a vagus nerve region of the user;
a brain wave measure part configured to measure brain waves of the user;
a genioglossus muscle stimulator;
a first connection cable; and
a second connection cable,
wherein the body comprises:
a frame provided in a symmetrical and elliptical shape and having a front surface, a back surface and a side surface, wherein a length of the frame in a first direction is shorter than a length of the frame in a second direction perpendicular to the first direction, the side surface has a first side and a second side opposite to the first side in the first direction, a third side and a forth side opposite to the third side in the second direction, and both the first side and the second side are concavely recessed toward a center, and the frame is configured to be attached to the user's neck, a vagus nerve stimulator located on the back surface of the frame, provided to comprise a plurality of electrodes for providing electrical stimulation to the vagus nerve region, and configured to be attached to the skin directly above the vagus nerve region located next to carotid artery of the user, a heart rate sensor located at a center of left and right symmetry of the frame on the back surface of the frame and configured to detect heart rates of the use, a manipulator located in the front surface of the frame and configured to receive a the user's command for controlling the brain wave measure part and the heart rate sensor, a plurality of connection ports formed on the side surface of the frame to transmit and receive signals, and a controller configured to generate a neurofeedback signal based on the brain waves of the user and the heart rates of the user, wherein the plurality of connection parts include a first port formed on the first side of the side surface and a second port formed on the third side of the side surface, wherein the genioglossus muscle stimulator is configured to be attached around the user's neck and configured to comprise an electrode for outputting electrical stimulation corresponding to the neurofeedback signal, wherein the first connection cable is configured to be connected to the first port of the plurality of connection ports to connect the body and the brain wave measure part to each other, wherein the second connection cable is configured to be connected to the second port of the plurality of connection ports and configured to connect the body and the genioglossus muscle stimulator to each other, wherein the plural electrodes of the vagus nerve stimulator are provided one by one on left and right sides in the symmetrical structure of the frame and, when the frame is configured to be attached to the user's skin, are disposed perpendicular to a direction of the vagus nerve, and wherein the plurality of electrodes of the vagus nerve simulator include a first electrode disposed on a left side of the back surface of the frame and a second electrode disposed on a right side of the back surface of the frame, and the first electrode and the second electrode are symmetrically arranged on the back surface of the frame with respect to the first direction, and the first electrode and the second electrode being arranged along the second direction.

2. The neurofeedback device according to claim 1, wherein the brain wave measure part is configured to be attached to a head of the user to measure the brain waves of the user; and wherein the brain wave measure part comprises:

a first band configured to have a predetermined width and provided in a form of extending and being attached over a part of the user's head past back of the user's ear from around the user's neck when connected to the body through the first connection cable;

a patch-type first brain wave sensor located at one end of the first band and configured to be detachably attached to a part of the user's head to measure the brain waves in a left prefrontal lobe Fp1 region of the user;

a second brain wave sensor located at a rear end of the first brain wave sensor and configured to be detachably attached to the part of the user's head to measure the brain waves in a right prefrontal lobe Fp2 region of the user;

a reference electrode located at a rear end of the second brain wave sensor and configured to be detachably attached around the user's ear to provide a reference signal for brain wave measurement;

a ground electrode located at a rear end of the reference electrode and configured to be detachably attached around the user's ear to provide a ground signal for brain wave measurement; and a first connector located at a rear end of the ground electrode and inserted into and connected to another end of the first connection cable.

3. The neurofeedback device according to claim 2, wherein a portion, on which the first brain wave sensor, the second brain wave sensor, the reference electrode and the ground electrode are disposed, of the first band has a circular shape having a larger diameter than the predetermined width.

4. The neurofeedback device according to claim 3, wherein the first connection cable comprises:

a first cable;

a first terminal located at one end of the first cable and provided with a protruding terminal to be inserted into the first port of the plurality of connection ports of the body; and a first socket located at another end of the first cable and configured to comprise a hole into which the first connector of the brain wave measure part is to be inserted.

5. The neurofeedback device according to claim 2, wherein the genioglossus muscle stimulator comprises:

a second band configured to be attached to a skin directly above a genioglossus muscle region of the user when connected to the body through the second connection cable;

a genioglossus muscle electrode located on a back surface of one end of the second band to provide the electrical stimulation to the user's genioglossus muscle region, and provided in a form of a patch to be attached to the skin directly above the genioglossus muscle; and a second connector located at another end of the second band to be inserted into and connected to the second connection cable.

6. The neurofeedback device according to claim 5, wherein the second connection cable comprises:

a second cable;

a second terminal located at one end of the second cable and provided with a protruding terminal to be inserted into the second port of the plurality of connection ports of the body; and a second socket located at another end of the second cable and provided with a hole into which the second connector is to be inserted.

* * * * *